US011768996B2

(12) United States Patent
Saripalli et al.

(10) Patent No.: US 11,768,996 B2
(45) Date of Patent: Sep. 26, 2023

(54) RAPID RECONCILIATION OF ERRORS AND BOTTLENECKS IN DATA-DRIVEN WORKFLOWS

(71) Applicant: Edifecs, Inc., Bellevue, WA (US)

(72) Inventors: Kanaka Prasad Saripalli, Danville, CA (US); Frank Lucas Wolcott, Seattle, WA (US)

(73) Assignee: Edifecs, Inc., Bellevue, WA (US)

( * ) Notice: Subject to any disclaimer, the term of this patent is extended or adjusted under 35 U.S.C. 154(b) by 853 days.

(21) Appl. No.: 16/393,760

(22) Filed: Apr. 24, 2019

(65) Prior Publication Data
US 2019/0325011 A1    Oct. 24, 2019

Related U.S. Application Data

(60) Provisional application No. 62/661,907, filed on Apr. 24, 2018.

(51) Int. Cl.
| | |
|---|---|
| *G06F 17/16* | (2006.01) |
| *G06F 40/151* | (2020.01) |
| *G06N 3/08* | (2023.01) |
| *G16H 50/70* | (2018.01) |
| *G06N 20/00* | (2019.01) |
| *G06F 11/07* | (2006.01) |

(52) U.S. Cl.
CPC ........ *G06F 40/151* (2020.01); *G06F 11/0766* (2013.01); *G06F 17/16* (2013.01); *G06N 3/08* (2013.01); *G06N 20/00* (2019.01); *G16H 50/70* (2018.01)

(58) Field of Classification Search
CPC .... G06F 16/22; G06F 16/215; G06F 11/0766; G06F 11/1004; G06F 40/151; G06F 17/16; G16H 40/20; G16H 10/60; G16H 50/70; G16H 15/00; G16H 80/00; G06N 3/08; G06N 20/00
See application file for complete search history.

(56) References Cited

U.S. PATENT DOCUMENTS

| | | | |
|---|---|---|---|
| 10,714,213 B2 * | 7/2020 | Stern | G16H 80/00 |
| 2013/0124292 A1 * | 5/2013 | Juthani | H04L 63/083 |
| | | | 705/71 |
| 2019/0149504 A1 * | 5/2019 | Norwood | H04L 43/045 |
| | | | 709/206 |
| 2019/0214128 A1 * | 7/2019 | Colister | G16H 40/40 |
| 2019/0247717 A1 * | 8/2019 | Winterbottom | A63B 24/0084 |
| 2020/0074287 A1 * | 3/2020 | Mody | G06N 3/063 |

\* cited by examiner

*Primary Examiner* — Marcin R Filipczyk
(74) *Attorney, Agent, or Firm* — Nixon Peabody LLP

(57) ABSTRACT

A unified framework for healthcare workflows to introduce multiple integrated approaches to error analysis. A first approach uses machine learning to extend probabilistic record linkage and apply it to the task of reconciliation, classifying changes between datasets as intentional or unintentional. A second approach uses process mining to extract maximum information about process diagrams and process bottlenecks.

10 Claims, 4 Drawing Sheets

| | ClaimID | Activity | Timestamp | Duration | Resource |
|---|---|---|---|---|---|
| $f_{swap,ST}(i,j,k,t,d) \leftarrow$ | $i$ | swap·$j,k$ | $t$ | $d$ | ST |

400

| ClaimID | Activity | Timestamp | Duration | Resource |
|---|---|---|---|---|
| $i$ | swap-$j,k$ | $t$ | $d$ | ST |

$f_{swap,ST}(i,j,k,t,d)$

FIG. 4

RAPID RECONCILIATION OF ERRORS AND BOTTLENECKS IN DATA-DRIVEN WORKFLOWS

PRIORITY CLAIM

The present application claims priority to U.S. Provisional Patent No. 62/661,907 filed Apr. 24, 2018, which is hereby incorporated by reference as if fully set forth herein.

BACKGROUND

There is a need in the healthcare industry to unify disparate sources of patient data to provide better care at lower costs, which requires integration of efficient workflows that span across systems generating such data, such as Payer, Provider and Social infrastructures. Given the pressures to contain costs, it is critical for hospitals, health care systems, and payers to develop highly efficient systems that can reconcile disparities across the system nodes quickly and accurately. The integration of administrative (claims processing) and clinical (visits and procedures) data sources is being done by Health Information Technology (HIT) companies. However, there is a need to improve the workflows by reducing inefficiencies (such as bottlenecks and delays) and errors that arise from reconciling disparities across such diverse source systems.

As an example, patient matching, such as enterprise master patient index or enterprise-wide master patient index (EMPI) in health IT is used to identify and match the data about patients held by one provider with the data about the same patients held either within the same system or by another system (or many other systems). Failure to reconcile patients across all of their data records can impede interoperability, leading to patient safety risks, revenue loss and decreased provider efficiency. In 2017, the U.S. Department of Health and Human Services Office of the National Coordinator for Health Information Technology organized the Patient Matching Algorithm Challenge, which led to an improved method and standard for patient matching including such capabilities as deduplication and linking to clinical data. The competitors performed a significant amount of manual review. Vynca, the winner of the competition, used a stacked model that combined the predictions of eight different models into one. The team reported they manually reviewed less than 0.01 percent of patient health records. Such record matching platforms can be improved further, and this is a huge need across the healthcare industry.

Furthermore, in the case of both administrative and clinical workflows, errors, inefficiencies and losses of revenue and health are significant problems. For example, reduction of patient delay in clinical processes depends on improving interfaces as patients are transferred from activity to activity or department to department. All such workflows may be modeled using data science and machine learning techniques for process mining and bottleneck mining. Given the pressures to contain costs, it is critical for hospitals and health care systems, as well as Payers, to develop highly efficient systems that can reconcile disparities across the system nodes quickly and accurately, and resolve bottlenecks and errors in near-real time (e.g., revenue leaks in an Encounter management process or delays in the Quote to Card process in Enrollment management).

BRIEF DESCRIPTION OF THE DRAWINGS

FIG. 4 illustrates an event log according to an embodiment of the invention.

DETAILED DESCRIPTION

Figure 1:
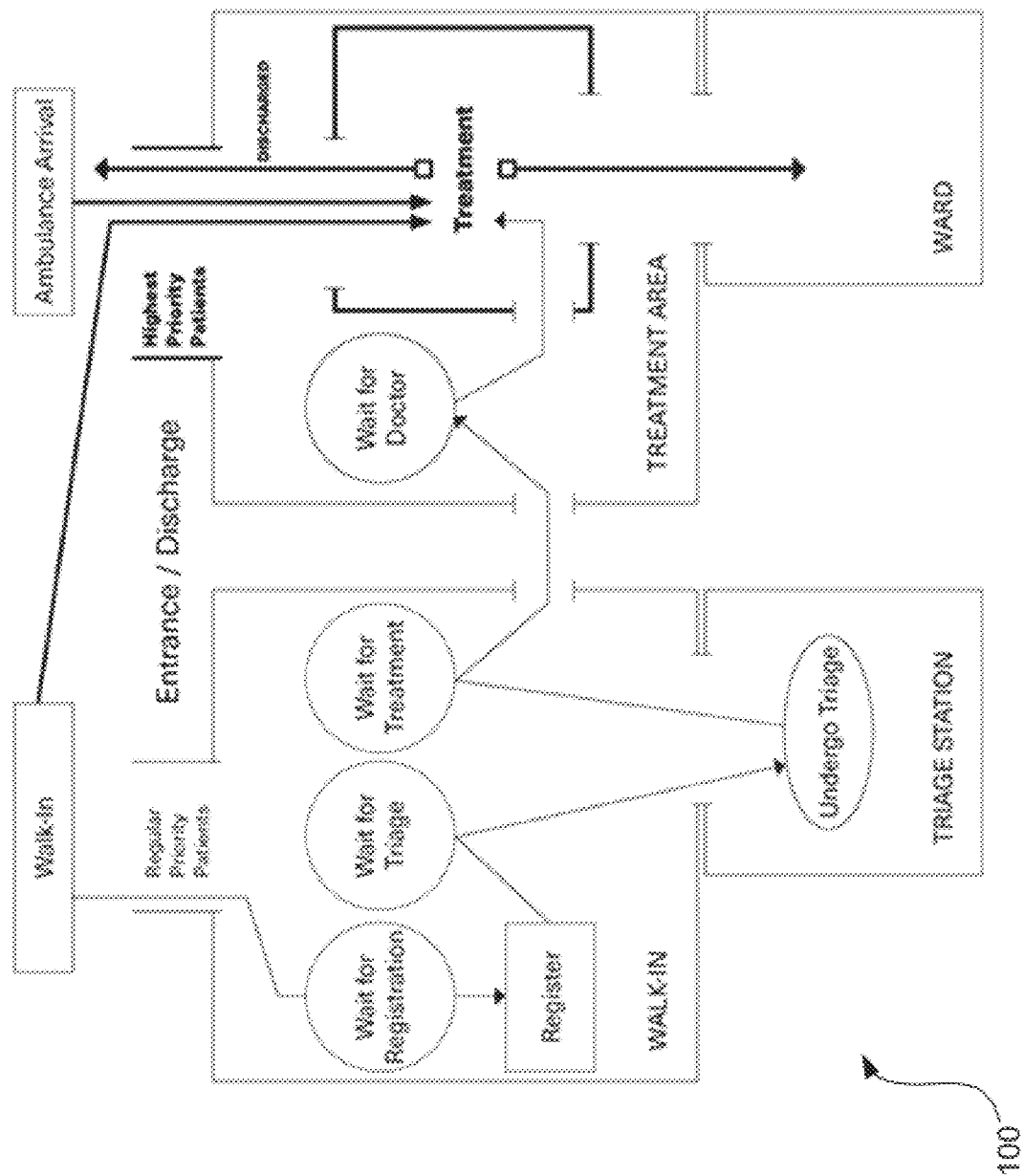
FIG. 1 illustrates an exemplary emergency department workflow diagram.

An embodiment includes a unified framework for healthcare workflows and uses it to introduce multiple integrated approaches to error analysis. A first approach uses machine learning to extend probabilistic record linkage and apply it to the task of reconciliation, classifying changes between datasets as intentional or unintentional. A second approach uses process mining to extract maximum information about process diagrams and process bottlenecks. This description includes the application of this framework to an example using administrative claims data.

A machine-learning (ML) solution and platform for the reconciliation of healthcare records, processes and bottlenecks would lead to, for example, the development of procedures to improve patient flow, to provide timely treatment and to maximize utilization of available resources. Patient flow analysis represents the study of how patients move through the health-care system.

One or more embodiments may include an error reconciliation framework that uses machine learning and process mining. In this approach, one or more embodiments define a health information exchange (HIE) workflow as a network diagram. At each node certain processes are executed, with a start time and end time. The workflow is bound by a service-level agreement (SLA) and can be mined using workflow related datasets as inputs for errors, discrepancies and bottlenecks.

One or more embodiments include the ability to:

characterize the reconciliation disparities by identifying where they may occur in a workflow, what data supports the workflow, and how the performance of the workflow may be influenced.

define and construct datasets for modeling the workflow processes and bottlenecks, such as delays in patient progress through care plan, errors and waste due to duplication of effort, and level of service (LOS).

develop ML algorithms for the characterization (i.e., mining) of such disparities and process bottlenecks, and for recommending remedial measures to address the same.

evaluate the models and metrics for a representative healthcare reconciliation solution.

Many healthcare workflows can be modeled by a directed graph $G=(V,E)$ of nodes $V$ and edges $E$, and a matrix $M_t$ of data flowing through this graph over a time interval $T$ For example, the "Quote to Card" workflow is a process involving various offices and their processing actions to enable a new patient, who is given a quote by a health insurance company ("Payer") for an insurance plan to actually receive the insurance card. Multiple organizations (each represented as a node in the graph) and their processing actions (represented as a link in the graph) would represent this workflow. Different $M_t$ matrices can be the dataframes that embody the member data and undergo transformations. As another example, insurance claims processing involves submission of claims from a doctor's office to the Payer, and a response back from the Payer to the Provider. Taken as a whole, the data forms a collection $M=\{M_t: t \in T\}$, which can be transformed into a numerical tensor M. Data transformations are applied to $M_t$ at the nodes, and the set of possible transformations $T=T_{int} \cup T_{unint}$ is divided into intentional transformations $T_{int}$ such as updating or adding to a record, and unintentional transformations $T_{unint}$ such as errors, corruptions, or dropped values. This application defines the unified framework (G,M,T) and uses it to introduce multiple integrated approaches to error analysis.

A first approach uses machine learning to extend probabilistic record linkage and apply it to the task of reconciliation, classifying changes between two data snapshots $M_a$ and $M_b$ as intentional or unintentional. Record linkage addresses the question of identifying matches or non-matches among pairs of records that are similar to varying degrees. For this purpose, researchers have developed a variety of indexing methods, encoders, and comparison functions. Whereas traditionally probabilistic record linkage used a methodology similar to Naive Bayes classification, and unrealistically assumed independence between covariates, in recent years machine learning algorithms like random forests and support vector machine (SVM) have been applied with improved results.

A pair of data snapshots $(M_a, M_b)$ at two times t=a and t=b is discussed below herein. An embodiment uses the record linkage literature and best practices to engineer morphological features that measure the similarities and differences between $M_a$ and $M_b$. These features are designed hierarchically—at the level of single entries, entire rows or columns, and the full matrix—to allow for scalability. Using these morphological features, an embodiment can train a classifier to understand changes in a dataset that are intentional from those that are unintentional errors.

A second approach to error analysis, also discussed below herein, uses process mining to extract maximum information about process diagrams and process bottlenecks. An embodiment uses the framework (G,M,T) to navigate between coarse- and fine-grained process diagrams.

These two approaches to healthcare workflow error analysis—reconciliation and process mining—compliment each other in both methodology and functionality. They amount to two ways of slicing and analyzing the data tensor M={$M_t$: t∈T}. Reconciliation allows for scalable batch analysis at user-determined checkpoints, and takes full advantage of advanced ML to identify unintentional errors and corruptions. Process mining discovers process diagrams and bottlenecks, to identify intentional data transformations that could be improved.

Discussed below herein is the underlying framework (G,M,T) in full detail. Also discussed below herein is dataset reconciliation, and process and bottleneck mining. In each discussion, applicant illustrates ideas with a running example using medical claims data processing. In the U.S., millions of healthcare claims are generated every day, and administrative costs of healthcare alone are estimated to be over $300 billion annually (or 15% of total healthcare costs). An improvement to modeling errors and reconciliation of such claims administrative workflows would lead to significant cost savings.

Referring to FIG. 1, consider a generic healthcare data workflow. In a clinical context, this could be the flow of patients through an emergency department 100. A single record corresponds to a patient with demographic and medical attributes. As the patient moves through the emergency department 100, their data is changed or updated as test results are recorded and procedures performed. In an administrative context, an example would be the medical claims processing workflow. A single record is a claim, moving between provider, payer, and the government as it is adjudicated, reworked, pended, appealed, and finally resolved and paid.

An embodiment can model such a workflow as a collection of matrices of data $M_t$—rows are records and columns are attributes—moving through a state diagram G through some time interval t∈T. The state diagram G=(V,E) may be a directed graph, such as a Petri net, consisting of a set V of vertices (nodes) and a set E of directed edges (arrows). It is convenient to represent the diagram using an adjacency matrix $A_G=(a_{ij})$, where $a_{ij}$ is one if there is a directed edge starting at $V_i$ and ending at $V_j$, and zero otherwise. One or more embodiments consider two types of state diagrams, corresponding to two levels of granularity: coarse and fine.

Major Resource State Diagram $G_{Coarse}$

Figure 2:
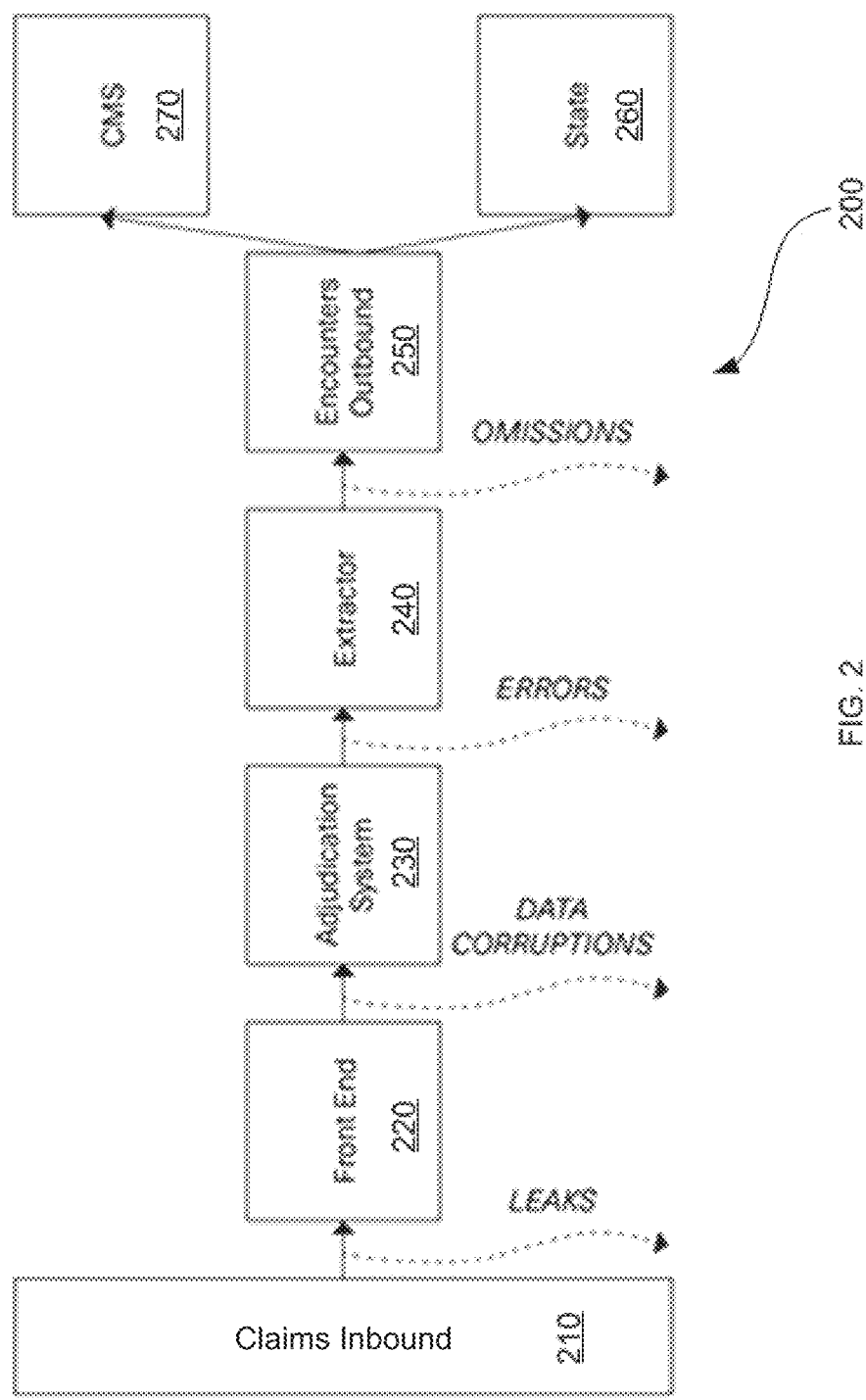
FIG. 2 illustrates a high-level state diagram tracking movement of healthcare data between major resources according to an embodiment of the invention.

FIG. 2 illustrates a high-level state diagram 200 tracking movement of healthcare data between major resources. In healthcare workflows, one or more embodiments may have an explicit high-level state diagram corresponding to movement of data between major resources. In the example of claims processing, this diagram might track the flow from provider 210, to a claims filing software 220 like Edifecs Smart Trading, to an insurance plan's adjudication system 230, to an extractor 240, to an encounter filing software 250 like Edifecs Encounter Management, to the state 260 or federal government 270, and back to the provider.

Record-Level Process Diagram $G_{Fine}$

Figure 3:
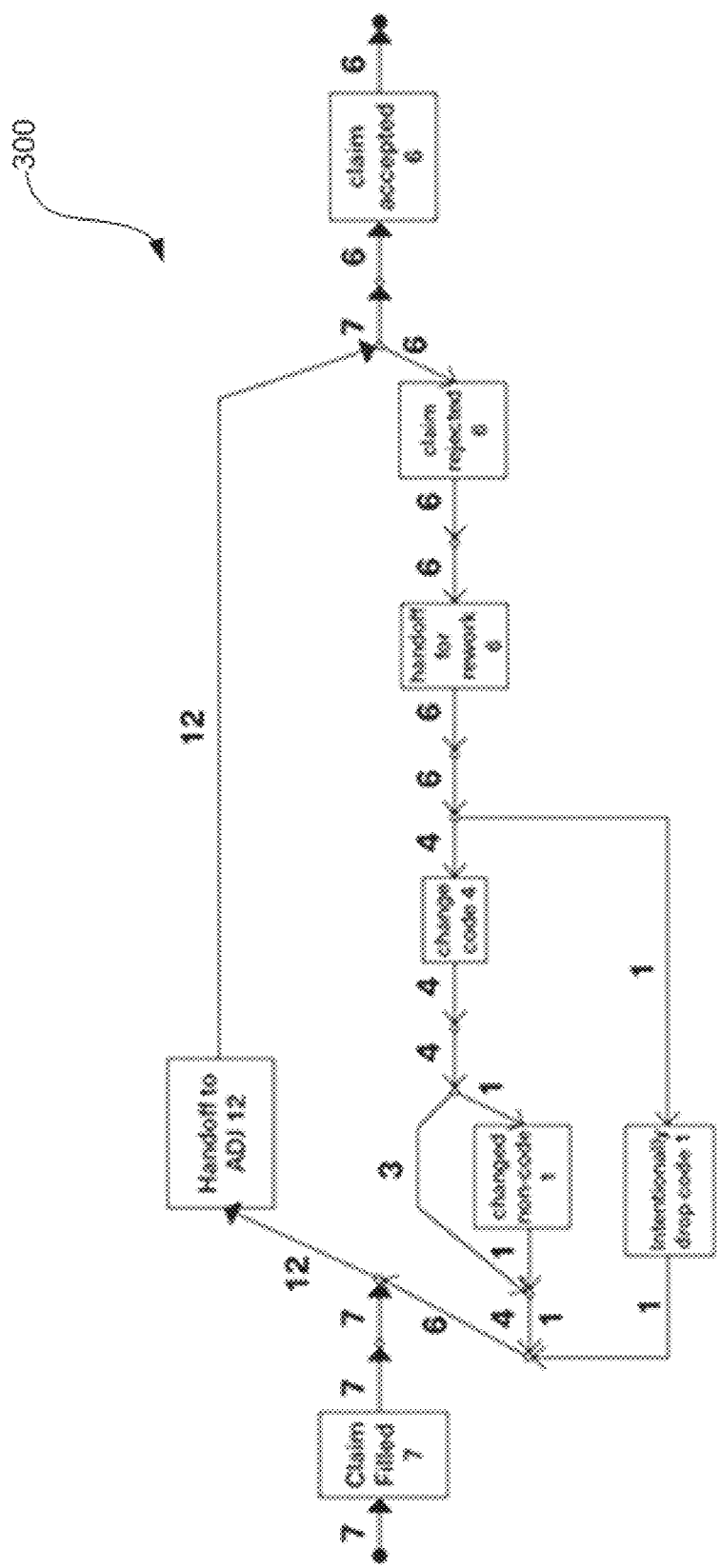
FIG. 3 illustrates an example of a petri net recording the sequence of events in the lifecycle of multiple medical claims according to an embodiment of the invention.

Portions of the application below herein will describe how event logs are associated to healthcare workflows, and will discuss process mining, which algorithmically generates a state diagram called a petri net from an event log. FIG. 3 illustrates an example of a petri net 300 recording the sequence of events in the lifecycle of multiple (e.g., seven) medical claims. The edge numbers record how many claims moved along each edge. At the level of an individual record, such as a claim that is being processed, there is a natural state diagram that tracks the actions and transformations applied to this record.

Assume that the records are tracked with a consistent unique identifier attribute, such as PatientId or ClaimId, whose values together form a set I. Assume that there is a static feature list F that captures all the attributes of the data that are provided, accessed, and changed in T Define the collection of matrices $$M=\{M_t:t\in T\}=\{(M_t)_{ij}:t\in T, i\in I, f\in F\}.$$

For a given t, one can refer to the data matrix $M_t$ as a dataset, or a data snapshot.

The feature set F can usually consist of a range of datatypes, so it is useful to consider a numerical encoding function μ: F→F that maps F to a set of numerical features F, for example by indexing string-type columns, and one-hot encoding categorical columns.

This allows one to convert M into a three-dimensional tensor M. However, in this application one can allow for non-numeric datatypes, and work mostly with M, which one can refer to as the data tensor.

Two Classes of Transformations

As the data flows through the state diagram G, it undergoes transformations. At a given node v∈V and time t∈T, the dataset $M_t$ is transformed by a matrix function $$f: Mt \to Mt+d,$$

where d is a time duration associated with the transformation. The transformations are drawn from a set $T=T_{int} \cup T_{unint}$, which is split further into intentional transformations $T_{int}$ and unintentional transformations $T_{unint}$.

An intentional transformation may affect values in a single row, or in a specific entry in a single row. They are drawn from a short list of actions, such as the following.
 add entry
 drop entry
 change entry (=drop+add)
 swap two entries Each intentional transformation has an explicit formula as a matrix function, and depends on what time it was applied, what row it was applied to, and what the action was. One can also attach meta-data, for example the resource/stage at which this transformation was applied. For example, if m=|I| and n=|F|, the transformation that swaps the entries in the jth and kth columns of the ith row of a m×n matrix X can be written $$f_{swap,ST}(i,j,k,t,d)(X)=X+(I_m{}^i)(X)(S^{jk}),$$

where $I_m{}^i$ is m×m with $(I_m{}^i)_{ii}=1$ and zeros elsewhere, and $S^{jk}$ is n×n with $(S^{jk})_{jj}=(S^{jk})_{kk}=-1$ and $(S^{jk})_{jk}=(S^{jk})_{kj}=1$ and zeros elsewhere. As described below, every intentional transformation is recorded in an event log.

The unintentional transformations may affect an entire row, an entire column, a single entry, or the full dataset $M_t$. They correspond to the introduction of errors and data corruptions, and are not recorded in any event log. Examples of unintentional transformations include the following.
 drop entry
 drop row (entire record)
 datatype of column is changed
 change between NA, NULL, Inf, NaN values
 error reading date format
 whitespace added to strings (before or after)
 character encoding changed
 Event Logs The combination of state diagram G, data tensor M, and transformations $T=T_{int} \cup T_{unint}$ constitute a flexible and generic framework for analyzing healthcare workflows. As discussed below, one can apply process mining within this framework, and so here we define an event log derived from (G,M,T).

As illustrated in FIG. 4, an event log 400 is a dataset recording events; each entry is a record of the activity (what happened) of a case (to whom/what) at a certain time (when). Additionally, it can include information on duration (how long) and resource (by whom/what).

Each element in the set of intentional transformations $T_{int}$ contains meta-data sufficient to append to an event log. When an intentional transformation is applied to a dataset $M_t$, we record this in the record-level event log E. For example, the swap transformation alluded to above could be recorded as illustrated in FIG. 4.

Thus, one can think of the event log E as equivalent to an enumeration of the data transformations in $T_{int}$. On the other hand, the transformations in $T_{unint}$ are unintentional and unrecorded; this is what one can use machine learning to detect as described herein below.

Morphology and Reconciliation

The field of record linkage, or entity resolution, is primarily concerned with classifying pairs of records $(r_1,r_2)$ as either a match or a non-match. For example, this is used in genealogy to resolve differences between historical records, or by the US Census to generate more accurate population statistics. Usually there are two thresholds, a high one above which confidence is high and the records are automatically matched, and a low one below which the records are definitely not matched. Pairs that fall in between these two thresholds are sent for manual reassessment. The records $r_1$ and $r_2$ share attributes, whose similarity is measured using a variety of comparison functions. Fellegi-Sunter pioneered probabilistic record linkage, but their formulation unrealistically assumes that the attributes are all independent. It has been shown that probabilistic record linkage is mathematically equivalent to Naive Bayes classification, which naturally suggests that other recent classification algorithms might be applied with improved results. This is indeed the case, and, recently, machine learning algorithms like SVM and random forests are applied to record linkage problems.

For two different times a, b∈T, with a<b we can look at the data snapshots $M_a$ and $M_b$, and compare them. If m=|I|, where I is the set of unique identifiers for records, and n=|F|, where F is the set of attributes, then $M_a$ and $M_b$ are both m×n matrices.

One can apply the tools of record linkage to the task of classifying changes in datasets as intentional or unintentional. To train supervised machine learning classification algorithms, one must have features and labels. Features according to at least one embodiment are morphological features such as similarity functions that capture the degree of similarity. Labels according to one or more embodiments are Intentional and Unintentional. The classification is done for a hierarchy of pairings derived from $(M_a,M_b)$, and aggregated into two reconciliation scores, as described below herein:

$S_{int}(a,b)$: a score 0-100 that measures how much the data changed from $M_a$ to $M_b$ through intentional transformations. A score of 0 indicates there were no intentional changes. A score of 100 indicates that all changes between $M_a$ and $M_b$ were intentional.

$S_{unint}(a,b)$: a score 0-100 that measures how much the data changed from $M_a$ to $M_b$ through unintentional errors and corruptions. A score of 0 indicates there are no errors, leakages, or corruptions between the datasets. A score of 100 indicates that every difference between $M_a$ and $M_b$ is unintentional.

The differences between $M_a$ and $M_b$ are captured in a hierarchy of pairings. The hierarchy is as follows.
 The pair $(M_a,M_b)$.
 For each identifier i∈I, the pair of rows $((M_a)_{ij}: j∈F,(M_b)_{ij}: j∈F)$.
 For each row i∈I and column j∈F, the pair of entries $((M_a)_{ij},(M_b)_{ij})$.
 Morphological Features Given a pairing $(r_1,r_2)$, one can build morphological features using the methods of record linkage, depending on the level in the hierarchy.

Use the numerical encoding function p to convert $(M_a, M_b)$ into matrices $(M_a,M_b)$ with numerical features (if this hasn't already been done), then use checksums. This determines whether or not there was any change to the full matrix.

Use checksums to detect if the row changed at all. Cast the two rows as strings and use string comparison functions (see below) to measure partial similarity.

Entry-by-entry comparison takes into consideration the datatypes.

Numeric. Use linear, exponential, or Gaussian similarity functions with offset.

String. Use Taro, Taro-Winkler, or Levenshtein comparison functions.

Date. Use several features that measure date similarity by considering swapping formats and changing levels of precision.

Neural Network and Reconciliation Scores

A feature of the reconciliation scores is a neural network trained to score changes between two rows as intentional or unintentional. Specifically, it is trained on data of the form $(r_a, r_b, c)$, where $r_a$ and $r_b$ are a pair of corresponding rows of two matrices $M_a$ and $M_b$, and $c \in \{\text{Int}, \text{Unint}\}$ is the label. From the pair of rows $(r_a, r_b)$ one can engineer morphological features, each of which is a real number between 0 and 1. These form the inputs to a neural network with two hidden layers and a 2-level softmax function in the output layer. Once trained, this model can take as input a pair of corresponding rows, say row i from a pair $(M_a, M_b)$, and output two scores between 0 and 1, which one can denote $S_{int}^i(a,b)$ and $S_{unint}^i(a,b)$. These measure the extent to which the changes between the rows were intentional and unintentional, respectively.

Using this trained neural network, one can calculate the reconciliation scores according to the following logic.

Given: two data snapshots $M_a$ and $M_b$, of size m×n.

Calculate checksums $(c_a, c_b)$ on numerical encoding $(M_a, M_b)$.

If $c_a = c_b$, set $S_{int}(a,b) = S_{unint}(a,b) = 0$ and exit.

Else, define p=0. For each row $i \in \{1, 2, \ldots, m\}$:
  (a) Let $(r_a^i, r_b^i)$ be the ith rows of $M_a$ and $M_b$.
  (b) Calculate checksums $(c_a^i, c_b^i)$ on $(r_a^i, r_b^i)$.
  (c) If $c_a^i = c_b^i$, set row scores $S_{int}^i(a,b) = S_{unint}^i(a,b) = 0$.
  (d) Else, set p=p+1. Feed $(r_a^i, r_b^i)$ into trained neural network to calculate row scores $S_{int}^i(a,b)$ and $S_{unint}^i(a,b)$.

Set $$S_{int}(a,b) = \frac{1}{p} \sum_{i=1}^{m} S_{int}^i(a,b) \text{ and } S_{unint}(a,b) = \frac{1}{p} \sum_{i=1}^{m} S_{unint}^i(a,b).$$

Getting Training Data

Training data according to an embodiment is a collection of tuples of data of the form $(r_a, r_b, c)$, where $r_a$ and $r_b$ are a pair of corresponding rows taken from two data snapshots $M_a$ and $M_b$, and $c \in \{\text{Int}, \text{Unint}\}$. Thus, one can build the training data by combining positive (Int) and negative (Unint) examples.

For the positive examples, one can apply single intentional transformation from $T_{int}$. That is, one can choose $a \in T$, $i \in I$, and some $f \in T_{int}$ that represents an intentional transformation that can be applied to the ith row $r_a^i$ of the matrix $M_a$. Then one can append the tuple $(r_a^i, f(r_a^i), \text{Int})$ to a training dataset.

For the negative examples, one can do something similar using an unintentional transformation from $g \in T_{unint}$ to append $(r_a^i, g(r_a^i), \text{Unint})$, although the unintentional transformations in $T_{unint}$ often affect multiple rows at the same time, so can be used to generate multiple negative examples.

Example with Claims Processing Data

An embodiment has implemented the reconciliation score computation using a small synthetic dataset of medical claims. The claims contain data fields common to actual claims, but drawing from a restricted set of possible procedure and diagnosis codes. Consistency requirements between codes, plan and provider type, and charge amount, are designed so that flawed claims could be filed, rejected, and reworked. Thus, one can construct a set of possible intentional transformations $T_{int}$, corresponding to valid claim rework steps, and a set of possible unintentional transformations $T_{unint}$ drawing from the lists given above.

One can then randomly apply valid transformations from $T_{int} \cup T_{unint}$ and collect labeled training data to train the row-wise neural network classifier, which fits into the reconciliation score algorithm described above. The implementation may be done in Python, using the Keras and TensorFlow libraries for the deep learning.

Process and Bottleneck Mining

Process mining is an established approach to extracting insights from event logs. An embodiment includes a collection of algorithms for process discovery and conformance analysis.

Process discovery takes as input an event log and algorithmically discovers a process diagram that best explains the processes underlying the event log. For example, an embodiment runs through the following paraphrased steps:

Scan the input event log L to collect $T_L$, the set of all possible activities.

Scan the event log to collect all start activities and end activities.

Collect $P_L$, the set of all the places, $p_{(A,B)}$, of the event log, where A and B are minimal subsets of events such that every event in A happens before every event in B, yet there is no causal dependency between pairs of events in A or pairs of events in B. Append a canonical start place $i_L$ and end place $o_L$.

Generate $F_L$, the natural set of directed arrows into places $\{(a, p_{(A,B)}): a \in A\}$ and out of places $\{(p_{(A,B)}, b): b \in B\}$. Append arrows from $i_L$ to all start activities and from all end activities to $o_L$.

Return $(P_L, T_L, F_L)$. These contain the data needed to render a process diagram.

There have been many enhancements of the α-algorithm, which take into consideration implicit places, incomplete logs, loops, and non-local dependencies. By taking into consideration activity frequencies, the algorithm can be made more robust to noise. The power of process discovery is in how it is data-driven, revealing the processes as they are, rather than how one may think they are.

Conformance analysis involves recombining a discovered process diagram with the original event log; one can replay the event log on the diagram. Bottleneck mining specifically looks at event timestamps of a replayed log, and gives insight into how much time is spent at each place in the process.

Example with Claims Processing Data

In an embodiment, every intentional transformation can be recorded in an event log, with realistic but random time durations. One can use process mining software to mine the event log and generate a petri net of the underlying processes. FIG. 3 is a rendering of one of the petri nets generated from claims processing dataset. One can then use plug-ins available to replay the event log on the petri nets and track sojourn times and bottlenecks.

This patent application is intended to describe one or more embodiments of the present invention. It is to be understood that the use of absolute terms, such as "must," "will," and the like, as well as specific quantities, is to be construed as being applicable to one or more of such embodiments, but not necessarily to all such embodiments. As such, embodiments of the invention may omit, or include a modification of, one or more features or functionalities described in the context of such absolute terms.

Embodiments of the present invention may comprise or utilize a special-purpose or general-purpose computer including computer hardware, such as, for example, one or more processors and system memory, as discussed in greater detail below. Embodiments within the scope of the present invention also include physical and other computer-readable media for carrying or storing computer-executable instructions or data structures. In particular, one or more of the processes described herein may be implemented at least in part as instructions embodied in a non-transitory computer-readable medium and executable by one or more computing devices (e.g., any of the media content access devices described herein). In general, a processor (e.g., a microprocessor) receives instructions, from a non-transitory computer-readable medium, (e.g., a memory, etc.), and executes those instructions, thereby performing one or more processes, including one or more of the processes described herein.

Computer-readable media can be any available media that can be accessed by a general purpose or special-purpose computer system. Computer-readable media that store computer-executable instructions are non-transitory computer-readable storage media (devices). Computer-readable media that carry computer-executable instructions are transmission media. Thus, by way of example, and not limitation, embodiments of the invention can comprise at least two distinctly different kinds of computer-readable media: non-transitory computer-readable storage media (devices) and transmission media.

Non-transitory computer-readable storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special-purpose computer.

A "network" is defined as one or more data links that enable the transport of electronic data between computer systems or modules or other electronic devices. When information is transferred or provided over a network or another communications connection (either hardwired, wireless, or a combination of hardwired or wireless) to a computer, the computer properly views the connection as a transmission medium. Transmissions media can include a network or data links which can be used to carry desired program code means in the form of computer-executable instructions or data structures and which can be accessed by a general purpose or special-purpose computer. Combinations of the above should also be included within the scope of computer-readable media.

Further, upon reaching various computer system components, program code means in the form of computer-executable instructions or data structures can be transferred automatically from transmission media to non-transitory computer-readable storage media (devices) (or vice versa). For example, computer-executable instructions or data structures received over a network or data link can be buffered in RAM within a network interface module (e.g., a "NIC"), and then eventually transferred to computer system RAM or to less volatile computer storage media (devices) at a computer system. Thus, it should be understood that non-transitory computer-readable storage media (devices) can be included in computer system components that also (or even primarily) utilize transmission media.

Computer-executable instructions comprise, for example, instructions and data which, when executed at a processor, cause a general-purpose computer, special-purpose computer, or special-purpose processing device to perform a certain function or group of functions. In some embodiments, computer-executable instructions are executed on a general-purpose computer to turn the general-purpose computer into a special-purpose computer implementing elements of the invention. The computer executable instructions may be, for example, binaries, intermediate format instructions such as assembly language, or even source code.

According to one or more embodiments, the combination of software or computer-executable instructions with a computer-readable medium results in the creation of a machine or apparatus. Similarly, the execution of software or computer-executable instructions by a processing device results in the creation of a machine or apparatus, which may be distinguishable from the processing device, itself, according to an embodiment.

Correspondingly, it is to be understood that a computer-readable medium is transformed by storing software or computer-executable instructions thereon. Likewise, a processing device is transformed in the course of executing software or computer-executable instructions. Additionally, it is to be understood that a first set of data input to a processing device during, or otherwise in association with, the execution of software or computer-executable instructions by the processing device is transformed into a second set of data as a consequence of such execution. This second data set may subsequently be stored, displayed, or otherwise communicated. Such transformation, alluded to in each of the above examples, may be a consequence of, or otherwise involve, the physical alteration of portions of a computer-readable medium. Such transformation, alluded to in each of the above examples, may also be a consequence of, or otherwise involve, the physical alteration of, for example, the states of registers and/or counters associated with a processing device during execution of software or computer-executable instructions by the processing device.

As used herein, a process that is performed "automatically" may mean that the process is performed as a result of machine-executed instructions and does not, other than the establishment of user preferences, require manual effort.

While the preferred embodiment of the disclosure has been illustrated and described, as noted above, many changes can be made without departing from the spirit and scope of the disclosure. Accordingly, the scope of the described systems and techniques is not limited by the disclosure of the preferred embodiment. Instead, the described systems and techniques should be determined entirely by reference to the claims that follow.

What is claimed is:

1. An electronic system comprising:
at least one non-transitory computer-readable memory storing machine-readable instructions; and
a control system including one or more processors configured to execute the machine readable instructions to:
receive as input an event log, the event log comprising entries describing activities performed in a healthcare-administration workflow, the start time of each of the activities, the end time of each of the activities and the place in the workflow at which each of the activities occurs;
determine from the event log a data set characterizing all of the activities performed in the workflow;
determine from the event log a data set characterizing the start time of each of the activities and the end time of each of the activities;
determine from the event log a data set characterizing the places in the workflow at which each of the activities occurs;
determine from the event log a starting place in the workflow and an ending place in the workflow;
based on the data sets, generate a diagram illustrating the places in the workflow and the activities of the workflow occurring in the places;

based on the data sets, generate a set of arrows in the diagram connecting the illustrated places in the workflow with each other according to the sequence of the activities performed in the workflow, the set of arrows beginning at the illustrated starting place in the workflow and terminating at the illustrated ending place in the workflow;

receive first and second datasets respectively including first and second record sets of a predetermined number, each of the first and second record sets including one or more associated record identifiers and one or more associated numerically represented dataset features, the second dataset resulting from one or more transformations of the first dataset by an entity, the one or more transformations each being one of an intentional transformation or an unintentional transformation;

generate first and second matrices based respectively on the first and second datasets, rows of the first and second matrices including the respective one or more record identifiers and columns of the first and second matrices including the one or more dataset features;

calculate a first checksum on the first matrix and a second checksum on the second matrix;

in response to determining that the first checksum does not equal the second checksum, calculate a third checksum on all rows of the first matrix and a fourth checksum on all rows of the second matrix;

in response to determining that the third checksum does not equal the fourth checksum, calculate, based on all rows of the first and second matrices, a first set of scores indicating that one or more of the transformations was intentional and a second set of scores indicating that one or more of the transformations was unintentional;

determine from the first and second set of scores which transformations were intentional and unintentional;

create the event log; and record only the intentional transformations in the event log.

2. The electronic system of claim 1, wherein the record identifiers comprise an identifier of a medical patient.

3. The electronic system of claim 1, wherein the record identifiers comprise an identifier of a medical insurance claim.

4. The electronic system of claim 1, wherein the data set features comprise a similarity function.

5. The electronic system of claim 1, wherein the event log comprises entries describing the activity, a subject of the activity and the time at which the activity occurred.

6. At least one non-transitory computer-readable medium on which are stored instructions that, when executed by at least one processing device, enable the at least one processing device to perform a method, the method comprising the steps of:

receiving as input an event log, the event log comprising entries describing activities performed in a healthcare-administration workflow, the start time of each of the activities, the end time of each of the activities and the place in the workflow at which each of the activities occurs, the activities being performed by one or more of health insurance entities, medical patients and physician offices;

determining from the event log a data set characterizing all of the activities performed in the workflow;

determining from the event log a data set characterizing the start time of each of the activities and the end time of each of the activities;

determining from the event log a data set characterizing the places in the workflow at which each of the activities occurs;

determining from the event log a starting place in the workflow and an ending place in the workflow;

based on the data sets, generating a diagram illustrating the places in the workflow and the activities of the workflow occurring in the places; and based on the data sets, generating a set of arrows in the diagram connecting the illustrated places in the workflow with each other according to the sequence of the activities performed in the workflow, the set of arrows beginning at the illustrated starting place in the workflow and terminating at the illustrated ending place in the workflow;

receiving first and second datasets respectively including first and second record sets of a predetermined number, each of the first and second record sets including one or more associated record identifiers and one or more associated numerically represented dataset features, the second dataset resulting from one or more transformations of the first dataset by an entity, the one or more transformations each being one of an intentional transformation or an unintentional transformation;

generating first and second matrices based respectively on the first and second datasets, rows of the first and second matrices including the respective one or more record identifiers and columns of the first and second matrices including the one or more dataset features;

calculating a first checksum on the first matrix and a second checksum on the second matrix;

in response to determining that the first checksum does not equal the second checksum, calculating a third checksum on all rows of the first matrix and a fourth checksum on all rows of the second matrix;

in response to determining that the third checksum does not equal the fourth checksum, calculating, based on all rows of the first and second matrices, a first set of scores indicating that one or more of the transformations was intentional and a second set of scores indicating that one or more of the transformations was unintentional;

determining from the first and second set of scores which transformations were intentional and unintentional;

creating the event log; and recording only the intentional transformations in the event log.

7. The at least one medium of claim 6, wherein the record identifiers comprise an identifier of a medical patient.

8. The at least one medium of claim 6, wherein the record identifiers comprise an identifier of a medical insurance claim.

9. The at least one medium of claim 6, wherein the data set features comprise a similarity function.

10. The at least one medium of claim 6, wherein the event log comprises entries describing the activity, a subject of the activity and the time at which the activity occurred.

* * * * *